US008916388B2

(12) United States Patent
Bergmann et al.

(10) Patent No.: US 8,916,388 B2
(45) Date of Patent: Dec. 23, 2014

(54) IN VITRO MULTIPARAMETER DETERMINATION METHOD FOR THE DIAGNOSIS AND EARLY DIAGNOSIS OF NEURODEGENERATIVE DISORDERS

(75) Inventors: Andreas Bergmann, Berlin (DE); Andrea Ernst, Hennigsdorf (DE); Harald Hampel, Munich (DE)

(73) Assignee: Sphingotec GmbH, Hennigsdorf (DE)

( * ) Notice: Subject to any disclaimer, the term of this patent is extended or adjusted under 35 U.S.C. 154(b) by 1557 days.

(21) Appl. No.: 12/305,088

(22) PCT Filed: Jun. 15, 2007

(86) PCT No.: PCT/EP2007/005299
§ 371 (c)(1),
(2), (4) Date: Sep. 28, 2009

(87) PCT Pub. No.: WO2007/144194
PCT Pub. Date: Dec. 21, 2007

(65) Prior Publication Data
US 2010/0062463 A1 Mar. 11, 2010

(30) Foreign Application Priority Data
Jun. 16, 2006 (DE) .......................... 10 2006 027 818

(51) Int. Cl.
*G01N 33/53* (2006.01)
*G01N 33/68* (2006.01)

(52) U.S. Cl.
CPC .... *G01N 33/6896* (2013.01); *G01N 2800/2821* (2013.01); *G01N 2800/28* (2013.01); *G01N 2800/2814* (2013.01); *Y10S 436/811* (2013.01)
USPC .......................................... 436/500; 436/811

(58) Field of Classification Search
None
See application file for complete search history.

(56) References Cited

U.S. PATENT DOCUMENTS

2010/0209433 A1* 8/2010 Bergmann et al. ......... 424/158.1

FOREIGN PATENT DOCUMENTS

WO WO 2004/059293 * 7/2004

OTHER PUBLICATIONS

Girgis et al (J Neurol Sci 99: 59-74,1990) abstract only.*
Silver (Current Opinion in Nephrology and Hypertension 15:14-21, 2006).*
Mukaddam-Daher (Expert Opin. Ther. Targets 10: 239-252, 2006).*
Daniels et al. (Heart Failure Clin.2: 299-309, 2006).*
Dietz, (Cardiovascular Res.,68: 8-17, 2005).*
Albadalejo et al.Rev Neurol 25: 139, 1997.*
Kondziella et al (Neuroreport 20: 825-827, 2009).*
Ewers et al (Exptl Gerontology 45: 75-79, 2010).*
Invitrogen protein microarray.*

* cited by examiner

*Primary Examiner* — Daniel E Kolker
*Assistant Examiner* — Aditi Dutt
(74) *Attorney, Agent, or Firm* — Millen, White, Zelano, Branigan, P.C.

(57) ABSTRACT

In vitro multiparameter method for the diagnosis and early diagnosis, for determination of the severity and for assessing the course and prognosis of neurodegenerative disorders, in which the concentrations of at least two different vasotropic peptides are determined in a biological fluid from a person suffering from subjective or objectively detectable cognitive impairments, the resulting person-specific measurements are combined computationally to give a person-specific complex reference value, and conclusions are drawn concerning the presence of a neurodegenerative disorder in the person on the basis of the person-specific complex reference value found.

7 Claims, 5 Drawing Sheets

IN VITRO MULTIPARAMETER DETERMINATION METHOD FOR THE DIAGNOSIS AND EARLY DIAGNOSIS OF NEURODEGENERATIVE DISORDERS

CROSS REFERENCE TO RELATED APPLICATIONS

This application is a 371 filing of PCT International application no. PCT/EP2007/005299 filed Jun. 15, 2007 and published in German as WO 2007/144194 on Dec. 21, 2007, which claims the priority of German application no. DE 102006027818.6 filed Jun. 16, 2006. The disclosures of these applications and all other patents, published applications and other references cited herein are hereby incorporated by reference in their entirety.

FIELD OF THE INVENTION

The present invention relates to a novel in vitro method for the diagnosis and in particular early diagnosis of neurodegenerative diseases, in particular of dementias, such as Alzheimer's disease and precursors thereof, in which a plurality of vasotropic or blood pressure-regulating substances are simultaneously taken into account as biomarkers, in particular combinations of vasodilatory and/or vasoconstrictive physiologically active peptides, when making the diagnosis.

BACKGROUND OF THE INVENTION

In the context of the present invention, the term "diagnosis" is used as an overall term for medical determinations which may be based on different problems according to the clinical condition of the patient (of the investigated person) for whom the determination is carried out and which serve for the detection and, in the present case, in particular also for the early detection, the determination of the severity and the assessment of the course, including the therapy-accompanying assessment of the course, and the prognosis of the future course of a disease. What is of particular importance in the present context is that a diagnosis may also be a negative diagnosis in which the presence of a certain disease is made improbable owing to the failure to establish certain features typical of the disease, for example the nondetectability of biomarkers or biomarker combinations associated with the relevant disease in a blood sample of a patient.

Biomarkers which can be found at elevated levels in the case of a plurality of different diseases and therefore by themselves do not permit a positive diagnosis of a specific disease—although as a rule they may also be decisive for the positive diagnosis on inclusion of further clinical or biochemical parameters—are also of great value for the negative diagnosis. Biomarker combinations therefore frequently permit statements which could not be made, or could not be made with the same probability, in the case of an isolated determination of only individual biomarkers or parameters.

The diseases regarding the diagnosis of which the present invention is concerned tend to be slowly developing, chronic neurodegenerative diseases of noninfectious etiology, in particular dementias.

Dementias are designated generally as diseases for which a common feature is the loss of acquired intellectual abilities, especially of memory, and of the normal personality level as a result of brain damage. Dementias are as a rule relatively slowly developing diseases of chronic character. If dementias occur prior to old age, in middle age, they are referred to as presenile dementias and they are differentiated on the basis of the symptoms and cerebropathological changes typical of them, in particular the following diseases or groups of diseases:

Alzheimer's disease (AD) is the most frequent neurodegenerative dementia, accounts for ⅔ of all cases of dementia and is also the practically most important field of use for the present invention. AD is distinguished by three important pathological features which however can be detected with certainty only post mortem: the formation of amyloid plaques and neurofibrillar bundles and the loss of nerve cells (for an overview cf. (1); literature references in the description in the form of numbers relate to the list of references following the description). Amyloid plaques consist of extraneuronal aggregates of the amyloid-β protein, while the neurofibrillar bundles contain mainly tau-protein and neurofilaments. It is presumed that the plaque and neurofibril formation is the cause of the death of nerve cells.

The most important symptoms of AD are increasing impairment of the capacity to register and disturbance of intellectual function in combination with relatively persistent emotional responsiveness, these symptoms being accompanied by further less specific disturbances which make it more difficult to distinguish AD from other forms of dementia.

Observations of AD patients and patients who develop AD in the course of their clinical observation over many years led to the formulation of criteria for mutually distinguishable groups of patients which cover the entire range of (a) persons without subjective and objective cognitive disturbances (which in the context of the present invention represent the control group) through
(b) patients who complain about subjective diminished cognitive ability but in whom no cognitive deficits can be found (in the context of the present invention, this is the group of "SCD" patients, where "SCD" represents "subjective cognitive disturbances"), further through
(c) patients who have been found to have mild cognitive disturbances and who have been diagnosed with "possible AD" ("pos AD") where no other dementia-causing diseases are present (in the context of the present invention, this is the group "MCD pos AD", where "MCD" represents "mild cognitive disturbances") to
(d) the group of patients with the typical clinical picture for considerable cognitive disturbances which have begun gradually and progress slowly, which patients are diagnosed with "probable AD" when other causes of dementia can be ruled out (in the context of the present invention, this is the group "pr AD", where the abbreviation represents "probable Alzheimer's").

Regarding the assignment of persons or patients with subjective and/or objective cognitive disturbances to various groups, reference is additionally made to (2), (3), (4) and (5).

Dementia with lewy bodies (DLB) is the second most frequent cause of a dementia after Alzheimer's disease. Neuropathologically, DLB is characterized by the occurrence of so-called lewy bodies in the brain stem and in the cortex. These lewy bodies predominantly comprise aggregates of the presynaptic protein (α-synuclein) and ubiquitin. The lewy body pathology can be associated to various extents with Alzheimer- and Parkinson-typical neuropathological changes. Thus, in the case of DLB too, the formation of beta-amyloid and senile plaques occurs, but not neurofibril bundles (for an overview, cf. (6)). Lewy bodies are also present in the brain of patients with Parkinson's disease, although in a different distribution.

The key symptoms of DLB are a progressive cognitive disturbance, episodes of confusion with fluctuating attentiveness and awareness, Parkinsonism, frequent falls and syncopes (brief, paroxysmal unconsciousness). The sensitivity and specificity of the diagnostic criteria are high throughout regarding the specificity but in some cases very low regarding the sensitivity. This means that DLB is frequently not diagnosed in day-to-day clinical routine.

Frontotemporal dementia (FTD) is also referred to as Pick's disease and accounts for about 20% of presenile dementias. FTD is in some cases of genetic origin and is among the so-called tauopathies, which are distinguished by overexpression or underexpression of a tau-protein subtype or by the expression of a mutated tau-protein. Neuropathologically, local atrophy of the frontal and/or temporal cortex and of the substantia nigra and of the basal ganglia occurs. This results in speech disturbances of varying severity, a personality change and behavioral abnormalities. Overall, FTD is underdiagnosed with a sensitivity of 93% and a specificity of only 23%, AD representing the most frequent misdiagnosis.

The term vascular dementia (VAD) summarizes diseases in which a dementia is triggered owing to blood flow disturbances in the brain. There are different types of VAD, of which multi-infarction dementia (MID) and subcortical VAD (also referred to as Binswanger's disease) are the most frequent forms.

Binswanger's disease is a slowly progressing dementia which is characterized pathologically by cerebrovascular lesions in the white brain substance. Clinically, this results in behavioral abnormalities, such as agitation, irritability, depression and euphoria, and slightly impaired memory.

Multi-infarction dementia occurs gradually as a result of a plurality of small strokes, also referred to as transient ischemic attacks (TIA), which led to the destruction of brain tissue in the cortex and/or subcortical areas. The strokes may also have remained completely unnoticed, in which case the dementia is the first noticeable consequence. When MID is present, there is a gradual decrease in cognitive abilities, associated with severe depressions, mood variations and epilepsy.

A diagnosis of dementia is carried out nowadays predominantly on the basis of neuropsychological investigations and observation of the development of the disease and its course, using exclusion criteria for certain forms of dementia. In very many cases, these investigations give ambiguous results, which explain the abovementioned numbers for the underdiagnosed forms of dementia or incorrectly diagnosed cases. The cerebral changes typical of the disease cannot of course be determined directly on living patients, and investigations of the brain functions using medical equipment by means of, for example, X-ray tomography or magnetic resonance imaging are complicated and expensive.

It would therefore be desirable to be able to supplement and thereby considerably improve the detection and in particular early detection of dementias by the measurement of informative biomarkers which can be determined, for example, in a blood sample (serum sample, plasma sample) of a patient with the aid of relatively simple test methods.

For the diagnosis of Alzheimer's disease, the Ronald and Nancy Reagan Institute of the Alzheimer's Association and the NIA Working Group published guidelines for the criteria which are set regarding an ideal biomarker for the detection of AD (7). The following criteria should ideally be fulfilled by the biomarker:
1. It should be brain-specific and detect a fundamental feature of the neuropathology of these diseases.
2. The diagnostic sensitivity and the specificity of at least 80% should exist.
3. The disease-specific change of the biomarker should manifest itself in as early a stage as possible of the disease, in order to be able to begin suitable therapeutic measures (8).

Up to the present, however, there is no biomarker which could be used in day-to-day clinical routine in the blood or the cerebrospinal fluid with sufficient certainty for the early and differential diagnosis of AD and fulfills all abovementioned criteria. At present, various potential marker candidates are being investigated, including inflammation markers, such as IL-6 and TNFα, markers for oxidative stress, such as 3-nitrotyrosine, and markers which are associated with characteristic pathological changes of AD, such as amyloid β, which is a main constituent of the amyloid plaques, and the tau-protein, which is a substantial constituent of the neurofibril bundles (cf. the overview in (8); (9)).

There is a current demand for supplementary investigative methods which provide valid laboratory findings and which are based on a determination of substances suitable as biomarkers for dementias, in particular for Alzheimer's disease (AD), in blood or plasma samples and are suitable for supporting an early positive diagnosis and/or for a negative diagnosis by exclusion in the case of persons who are suspected of having a dementia, in particular AD.

SUMMARY OF THE INVENTION

The present invention provides such an investigative method in the form of an in vitro multiparameter method for the detection and early detection, for the determination of the severity and for the assessment of the course and prognosis of neurodegenerative diseases, in which the concentrations of at least two analytes which are selected from the group consisting of the vasotropic peptides are determined in a biological fluid of a person who is suffering from subjective or objectively detectable cognitive disturbances, the person-specific measured values obtained for the respective concentrations of the at least two analytes determined are combined computationally to give a person-specific complex reference value and conclusions regarding the presence of a neurodegenerative disease in the person or an early form typical of said disease, or regarding the course of the disease and/or the success of the efforts to alleviate or prevent it, are drawn on the basis of the person-specific complex reference value determined.

The group consisting of the vasotropic peptides comprises a first subgroup consisting of the vasodilatory peptides and a second subgroup consisting of the vasoconstrictive peptides.

In the computation evaluation, person-specific measured values for the concentrations of the measured vasotropic peptides of the same subgroup are combined with the same ranking, preferably by multiplication, and person-specific measured values for concentrations of vasotropic peptides of different subgroups are preferably combined by division.

The concentrations of the vasotropic peptides are preferably determined by determining the concentrations of physiologically inactive propeptide fragments, which are released from coordinated propeptide precursors and are not the actual vasotropic peptide, in the biological samples investigated, in particular in serum or plasma.

Vasodilatory peptides determined are preferably the natriuretic peptides ANP, BNP and/or CNP and/or the peptide adrenomedullin and/or the peptide CGRP (calcitonin gene-related peptide) and vasoconstrictive peptides determined are an endothelin, in particular endothelin 1 (ET-1). However, the method according to the invention can also be modified by determining or concomitantly determining other vasotropic analytes which can be assigned to the two abovementioned subgroups, in addition to or instead of said peptides. Firstly the peptides of the renin-angiotensin-aldosterone (RAA) system, in particular the vasoconstrictive peptide angiotensin II, and arginine vasopressin (AVP), substance P (SP), and secondly the vasodilatory peptides $CGRP_{1-37}$, amylin (IAPP), endothelin-3 (ET-3) and the vasoactive intestinal peptide (VIP) may additionally be mentioned in this context. Furthermore, it may also be mentioned that further nonpeptide analytes, such as NO (for example, determinable as nitrite or nitrate), may be taken into account concomitantly. For supplementary information or regarding further literature on said individual potential analytes, reference is made to (10) and (11). In addition, reference is made expressly to the known further pairs of vasotropic substances which are mentioned in (10) and (11) and are involved with opposite actions in the same physiological control process.

The determination of the respective analytes in a biological fluid is preferably effected in whole blood, serum or plasma.

The concentration of ANP is preferably determined as the concentration of a proANP fragment with the aid of an assay of the applicant which detects a midregional segment of proANP (MR-proANP). Such an assay is described in EP 1 562 984 B1 and in (12).

The concentration of adrenomedullin (ADM) is preferably determined as the concentration of a midregional proADM fragment (MR-proADM) which comprises the aminoacids 45-92 of pre-proadrenomedullin. A suitable assay is described in EP 1 488 209 B1 and WO 2004/090546 and in (13).

The concentration of endothelin 1 (ET-1) is preferably determined as the concentration of a C-terminal ET-1 fragment (CT-proET-1) which comprises the aminoacids 168-212 of pre-proendothelin 1. A suitable assay is described in 1 564 558 B1 and WO 2005/078456 and in (14).

The determination of the at least two analytes is preferably carried out with the aid of immunodiagnostic assay methods in the form of aminoassays of the sandwich type, for example using one of the abovementioned assays of the applicant.

According to a preferred embodiment of the method according to the invention, the measured value for the concentration of one of the abovementioned vasodilatory peptides, or the value obtained by computational multiplication of at least two measured values for the concentrations of at least two vasodilatory peptides, is divided by the concentration for the vasoconstrictive peptide ET-1 for determining the patient-specific reference value.

The neurodegenerative disease whose improved diagnosis forms the subject matter of the present invention is in particular a dementia which is selected from a group consisting of Alzheimer's disease (AD), dementia with lewy bodies (DLB), frontotemporal dementia (FTD) and various forms of vascular dementia (VD), the method preferably being carried out as part of Alzheimer's diagnosis for detecting early forms of Alzheimer's disease (AD).

The in vitro multiparameter determination according to the invention can be carried out in routine clinical application on a relatively large scale, expediently also as a simultaneous determination by means of a chip technology measuring apparatus or in a so-called point-of-care (POC) determination using an immunochromatographic measuring apparatus. The determination and evaluation of the complex measured result of the multiparameter determination is expediently effected with the aid of a suitable computer program.

When the term "concentration" is used in this application, this term is not limiting in the sense that it does not mean only the steady-state concentration of the actual vasotropic peptide which can be measured in the biological sample.

The most important pathophysiologically released vasotropic peptides discussed in the present invention are present only to a relatively small extent so as to be measurable freely or unhindered in biological fluids. Important parts of the pathophysiologically released vasotropic peptides are rapidly abstracted from the biological fluid by binding two receptors and other membrane or vascular structures and/or are degraded.

The measurement of inactive copeptides formed from the same precursor propeptides, as is preferably effected according to the present invention with the use of the applicant's assays mentioned herein, reflects, in contrast to the instantaneous concentration of a biological fluid, the release of the vasotropic peptides in the sense of "active concentrations" over a relatively long time segment and also permits indirect concomitant detection of bound or rapidly degraded fragments of the vasoactive peptide released. In conjunction with the higher stability of such copeptides, this leads to higher measurable absolute concentration values for the analytes to be determined in the biological fluid, e.g. in serum or plasma.

However, the concentrations discussed in the present invention are not necessarily only the measurable concentrations of such inactive copeptides but may also be the concentrations of other measurable analytes, e.g. small molecules, such as NO, which are formed in each case in a ratio substantially proportional to the concentrations measurable for said inactive copeptides or are present in the biological fluid. Such analytes present in a biological fluid (serum, plasma) in a ratio proportional to the vasotropic peptides or copeptides may be regarded as "surrogate vasotropic peptides", the determination of which may be equivalent to the direct determination of the vasotropic peptides or of the corresponding copeptides and in the same way can give values which can replace the measured values for the concentrations of the vasotropic peptides or of the copeptides in the multiparameter determination according to the present invention. The indirect determination of the vasotropic peptides by determining such "surrogate vasotropic peptides" is intended to be covered by the general term "determination of the concentration of vasotropic peptides".

In the case of diseases which tend to have a chronic course without sudden deteriorations or improvements in the condition of the patient, as is the rule with dementias, there is, for example, a high probability that an only slightly variable steady-state overall condition which changes only slowly will develop with regard to the various disease-relevant analytes. In such a case, the steady-state concentrations of an active analyte, in the present case of a vasotropic peptide, measurable in the biological fluid of the patient should be substantially proportional to the amounts of the same analyte which are pathophysiologically released over relatively long periods, as can be measured in the form of the physiologically inactive copeptide. This means that those deviations of the control values of healthy persons which are detectable in the preferred multiparameter determination of inactive copeptides according to the present invention, and the course of these deviations which is typical of the disease, should also as a rule be reflected in the generally lower steady-state concentrations of the active analytes, so that the specific choice of the measured "analyte concentrations" should have no decisive qualitative influence on the diagnostic evaluation.

The present invention is based on considerations by the inventors to improve the diagnosis of dementias by making use of the knowledge that the known forms of dementia which are explained in more detail at the outset are also accompanied—to different extents—by inflammatory processes and endothelial damage, which are regarded as essential for the development, the symptoms and the course of the dementias, and it is for this reason that neurodegenerative diseases can also be regarded as neuroinflammatory disease.

Thus, Alzheimer's disease is characterized, inter alia, by the occurrence of chronic local inflammatory reactions in the brain with participation of various inflammatory proteins, such as complement factors, acute phase proteins and proinflammatory cytokines (9).

Inflammatory processes also play a role in the origin of vascular dementias (VAD). The levels of TNFα, TGFβ, IL-6 and GM-CFS (granulocyte-macrophage stimulating factor) are substantially increased in patients with VAD (15, 16).

In the case of DLB, too, inflammatory processes appear to play a role. Thus, the number of activated microglia cells in the brain of patients with DLB is increased, and proinflammatory cytokines, such as TNFα, are overexpressed in certain brain regions, such as the amygdala and the hippocampus.

On the other hand, there is only information in isolated cases regarding the occurrence of inflammatory reactions in the brain of FTD patients.

Starting (i) from the hypothesis that the neuroinflammatory processes associated with dementias lead to endothelial stress and blood flow disturbances, in particular to microcirculation disturbances of the brain, and (ii) that to this extent there is a similarity with cardiovascular diseases which are associated with blood flow disturbances or disturbances of the microcirculation of the heart tissue, and (iii) from exploratory analytical findings which show that increased formation of various vasotropic peptides is detectable in the case of such cardiovascular diseases, and finally (iv) using the improved analytical possibilities for the determination of the concentrations of various vasotropic peptides in reliable and in clinically valid form with the aid of novel immunoassays of the applicant in which a determination of physiologically inactive peptide fragments of the propeptide precursors of vasotropic peptides is carried out, the inventors investigated the question as to whether indications of elevated concentrations of such peptides can also be found in the plasma in the case of patients with different extents of cognitive disturbances, who have otherwise suffered from no known disease associated with increased production of vasotropic peptides.

Initial investigations by the applicant show that the vasodilatory peptides ANP, BNP and CNP and also adrenomedullin (ADM) are found at significantly increased levels in patients with various dementias, in particular in patients with Alzheimer's disease (AD patients). These analytical findings form the subject matter of the still unpublished prior German patent applications of the applicant with the application numbers 10 2005 036 094.7 of 1 Aug. 2005 and 10 2006 023 175.9 of 17 May 2006, respectively. Where a determination of ANP (as MR-proANP) or of ADM (as MR-proADM) in patient plasmas is effected in the present application, such a determination is effected in the manner described in said prior patent applications of the applicant.

That there may be a relationship between adrenomedullin production and microcirculation is known from (17). However, dementias are not discussed in this context.

Where attempts to measure natriuretic peptides in persons who showed dementia-like symptoms were described in the literature, no significant correlation had been found (18, 19).

The measured results, described below in the experimental section, in EDTA plasma samples of 60 apparently healthy normal persons (symptom-free controls) and 196 patients with mild to severe cognitive disturbances according to the groups (b) to (d) described at the outset gave for the first time a clear, diagnostically significant correlation between the concentrations found for, for example, MR-proADM and in particular MR-proANP and the severity of the dementia symptoms in the form of cognitive disturbances, the measured concentrations correlating in a significant manner with the severity of the disturbances and hence the AD precursors and thus being able to contribute to the differentiation of the various patient groups.

A parallel determination of CT-ET-1 gave lower measured values for dementia patients compared with healthy normal persons (controls), which measured values, however, did not clearly reflect the above course, such as, for example, the measured values for MR-proANP.

However, according to the present invention it was found that a further substantial improvement in the significance of the overall measurement in the context of a multiparameter measurement was obtained when the measured values for, for example, ANP(MR-proANP) and/or ADM (MR-proADM) were combined in a suitable manner with those of a measurement of CT-ET-1, in particular in the sense that the values for the vasodilatory peptides MR-proANP or MR-proADM which were measured for a certain patient or optionally the combined value obtained by multiplication of the values for MR-proANP and MR-proADM were related to the values for the vasoconstrictive peptide ET-1 (measured as CT-proET-1) which were measured for in each the same patient, by dividing the values for the measured concentrations of the vasodilatory peptides or for the mathematical product thereof by the values for CT-ET-1.

Because the patient-specific values for the vasodilatory peptides were thus related for evaluation purposes not only to an external cut-off value, which represents a statistical result of the measurement of corresponding analyte concentrations in the case of a relatively large heterogeneous group of patients and controls, but initially to a patient-specific internal reference value in the form of a measured value for at least one relevant vasoconstrictive peptide measured in the case of the same patient, in particular for CT-proET-1 herein, which will be regarded as an expression of an internal and individually variable patient status or patient standard, the significance of the measurement of the vasodilatory peptides once again increases considerably.

If the complex reference values obtained in the case of such an evaluation are related to corresponding average values obtained, for example, in the case of a group of controls or of patients with other diseases or with a different severity of the disease, in particular the sensitivity of the overall determination increases considerably.

This finding is explained in more detail below in the experimental section with reference to several figures and two tables.

Although the investigations were limited to date to plasma samples of patients who showed signs of precursors of AD or who had been diagnosed with "probably Alzheimer's disease", the inventors assume that—possibly with different typical concentration ranges—characteristic changes in the concentrations of vasotropic peptides in patient plasmas could be detectable also in the case of other neuroinflammatory forms of dementia, in particular in the case of vascular dementia (VAD) and dementia with lewy bodies (DLB).

The assay method used for the measurements described in the experimental section for MR-proANP, MR-proADM and CT-pro-ET-1 in patient plasmas was effected using the above-mentioned assays of the applicant which are described in the literature mentioned there and all of which are by their very nature non competitive immunoluminometric sandwich assays.

Reference is expressly made to the general statements on the problems of the determination of ANP or ADM or ET-1 in patient samples and the explanations for carrying out the assay in said patents or the publications (12, 13, 14), for supplementing the statements in the present application.

In the case of an additional, supplementary determination of the concentrations of the vasoconstrictive peptide arginine vasopressin (AVP), it is advisable to use an assay with which the propeptide fragment copeptin is determined and which is described in more details in WO 2006/018315 or in (20).

BRIEF DESCRIPTION OF THE DRAWINGS

Below, the invention is explained in more detail with reference to measured results and five figures.

DETAILED DESCRIPTION OF THE INVENTION

Experimental Section
Assay Description

The measurement of MR-proANP in plasma was effected using an immunoluminometric sandwich assay substantially as described in the experimental section of the abovementioned WO 2004/046181 (copending U.S. application Ser. No. 10/535,875), the contents of which are hereby incorporated by reference or in reference (12).

The measurement of MR-proADM in plasma was effected using an immunoluminometric sandwich assay substantially as described in the experimental section of the abovementioned WO 2004/090546 (copending U.S application Ser. No. 10/551,298 the contents of which are hereby incorporated by reference or in reference (13).

The measurement of CT-proET-1 in plasma was effected using an immunoluminometric sandwich assay substantially as described in the experimental section of the above mentioned WO 2005/078456 (copending U.S. application Ser. No. 10/588,746), the contents of which are hereby incorporated by reference or reference (14).

The measurement of MR-proANP, MR-proADM and CT-pro-ET-1 in the plasma of healthy controls and patients with cognitive disturbances of various severities For determining a reference value for the concentration of the respective analyte, a measurement was carried out in EDTA plasmas of 60 symptom-free control persons who neither showed symptoms of cognitive disturbances nor suffered from any other detectable disease (cardiovascular diseases; severe infection or inflammation), for whom it is known that elevated levels of the abovementioned biomarker analytes can be measured in them. For the control group, median values were determined for the measured concentrations as follows:

| | |
|---|---|
| MR-proANP = | 62.3 pmol/l |
| MR-proADM = | 0.60 nmol/l |
| CT-proET-1 = | 68.0 pmol/l |

Patients with dementia symptoms in the form of cognitive disturbances of various severities, on the basis of which an assignment of the individual patients to one of the abovementioned groups (b), (c) or (d) was made, served as a patient group.

Figure 1:
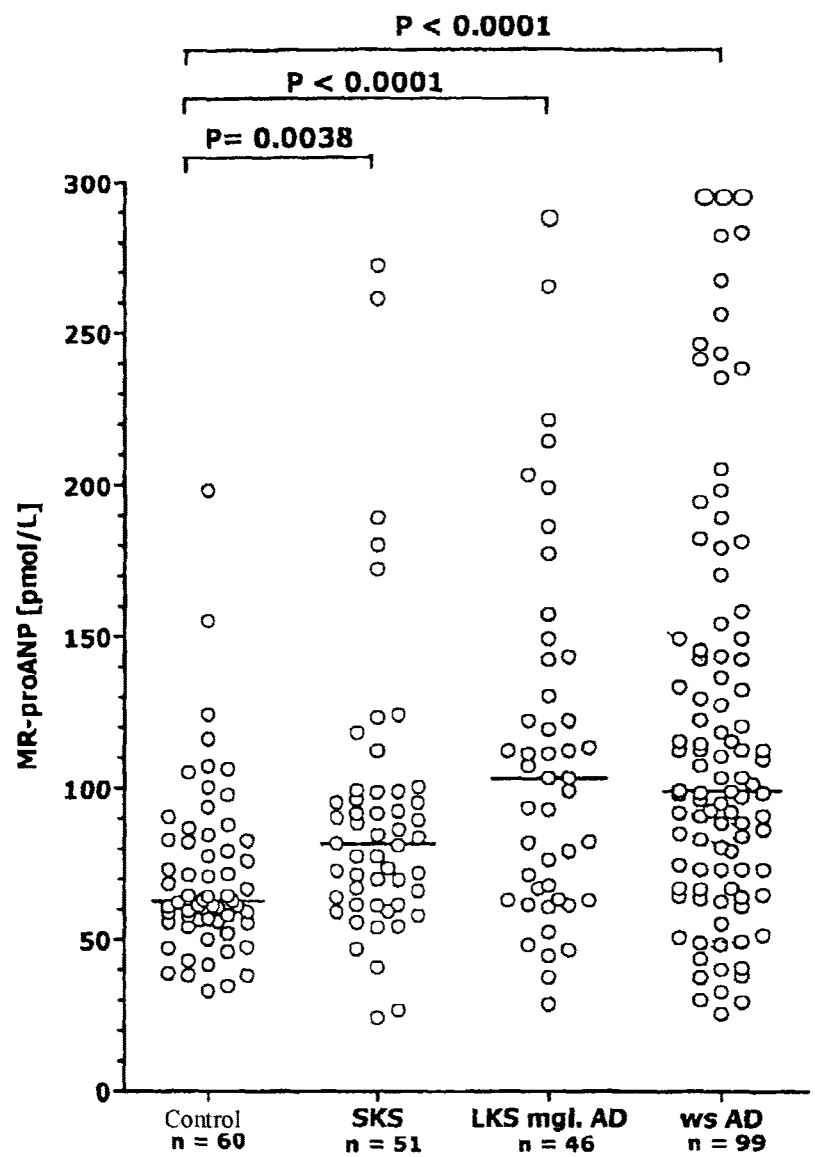
FIG. 1 shows the results of the measurement of the MR-proANP concentrations in EDTA plasmas of 60 healthy control persons and of 196 patients with cognitive disturbances of various severities, who corresponded to the abovementioned groups (b), (c) and (d), i.e. the groups "SCD" (51 patients), "MCD pos AD" (46 patients) and "pr AD" (99 patients).
Figure 2:
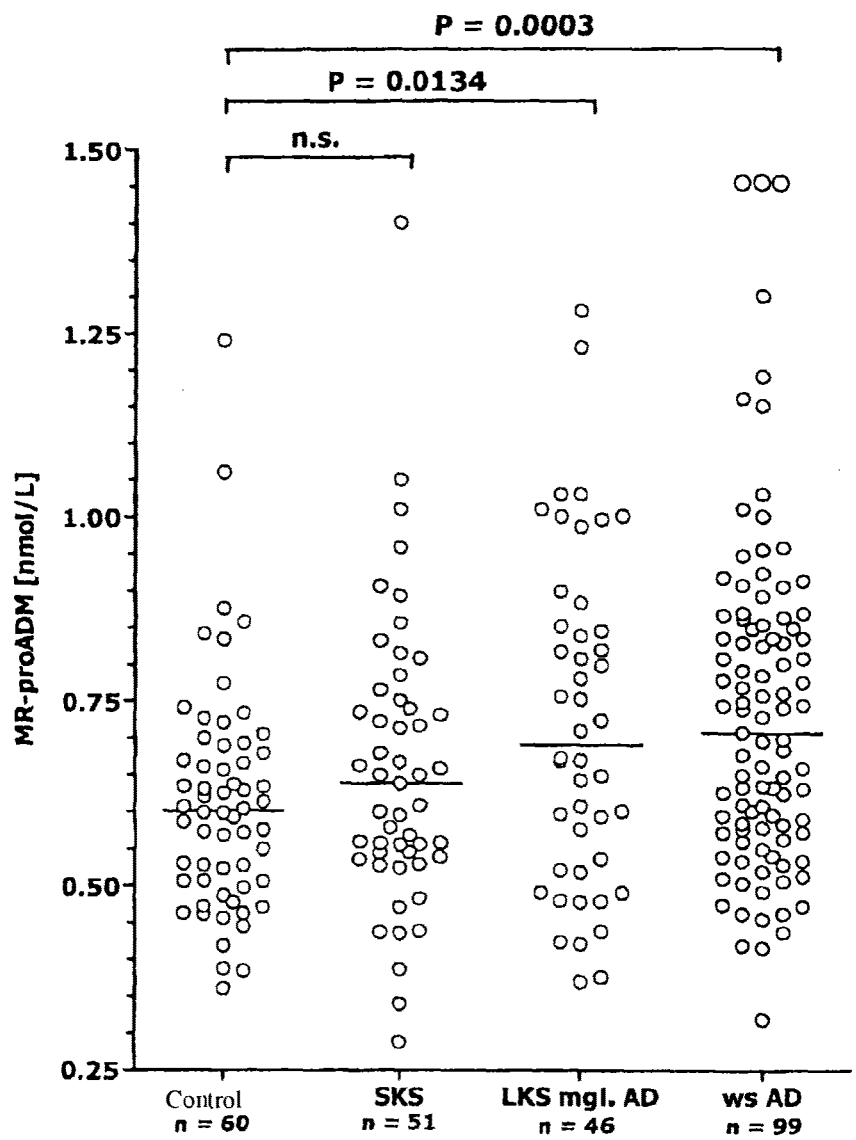
FIG. 2 shows the results of the measurement of the MR-proADM concentrations in EDTA plasmas of 60 healthy control persons and of 196 patients with cognitive disturbances of various severities, who corresponded to the abovementioned groups (b), (c) and (d), i.e. the groups "SCD" (51 patients), "MCD pos AD" (46 patients) and "pr AD" (99 patients).
Figure 3:
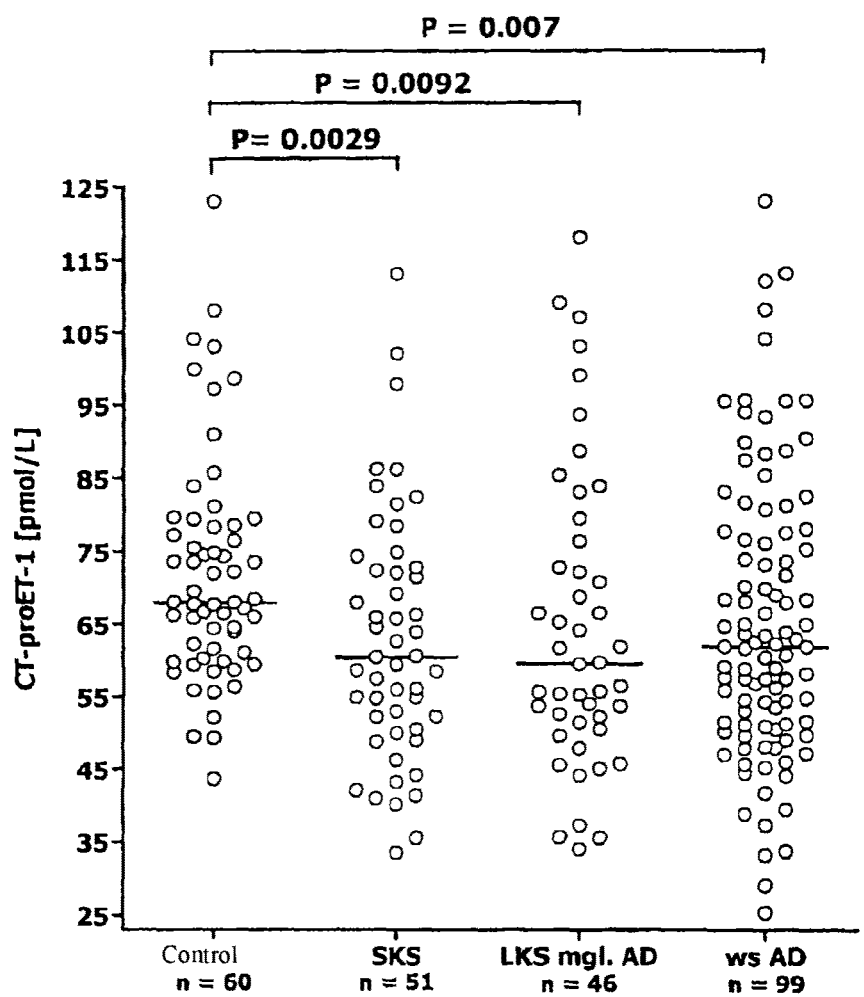
FIG. 3 shows the results of the measurement of the CD-proET-1 concentrations in EDTA plasmas of 60 healthy control persons and of 196 patients with cognitive disturbances of various severities, who corresponded to the abovementioned groups (b), (c) and (d), i.e. the groups "SCD" (51 patients), "MCD pos AD" (46 patients) and "pr AD" (99 patients).
Figure 4:
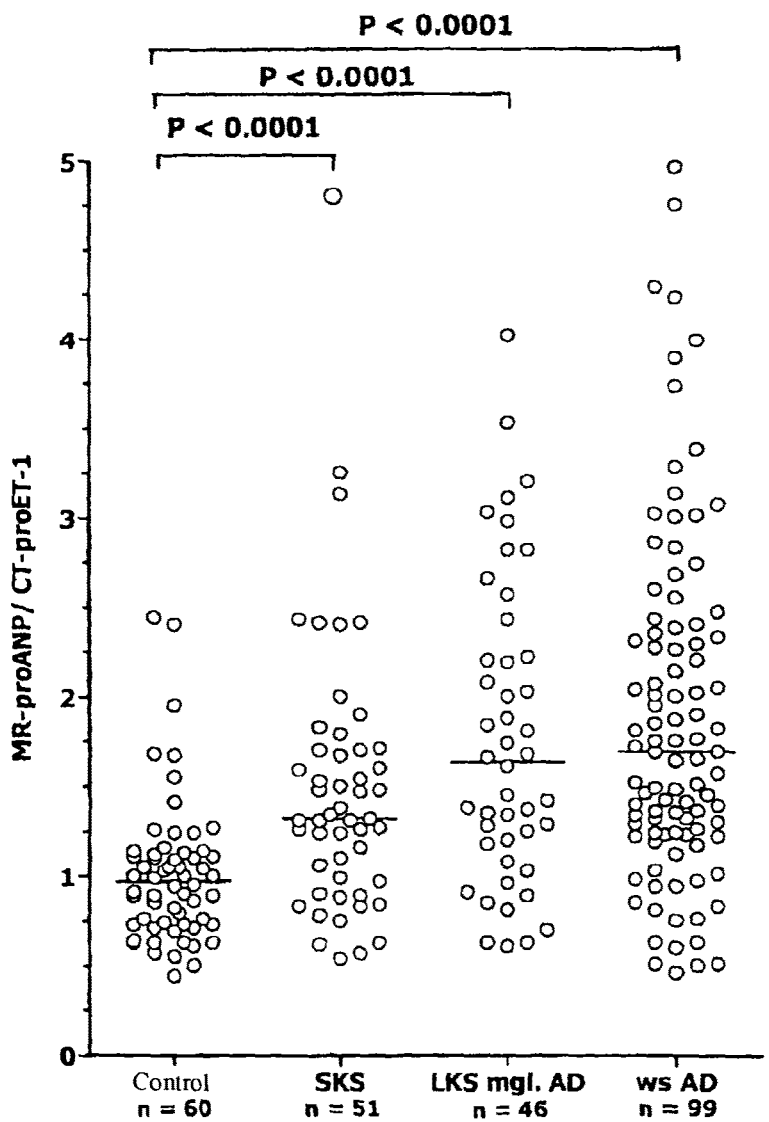
FIG. 4 shows the results of a common computational evaluation of the measured results, shown in FIG. 1, for the MR-proANP concentrations when these were related by calculating the quotient to the measured results for the CT-proET-1 concentrations in the same individual patients, shown in FIG. 3, in particular once again of 60 healthy control persons and of 196 patients with cognitive disturbances of various severities, who corresponded to the abovementioned groups (b), (c) and (d), i.e. the groups "SCD" (51 patients), "MCD pos AD" (46 patients) and "pr AD" (99 patients).
Figure 5:
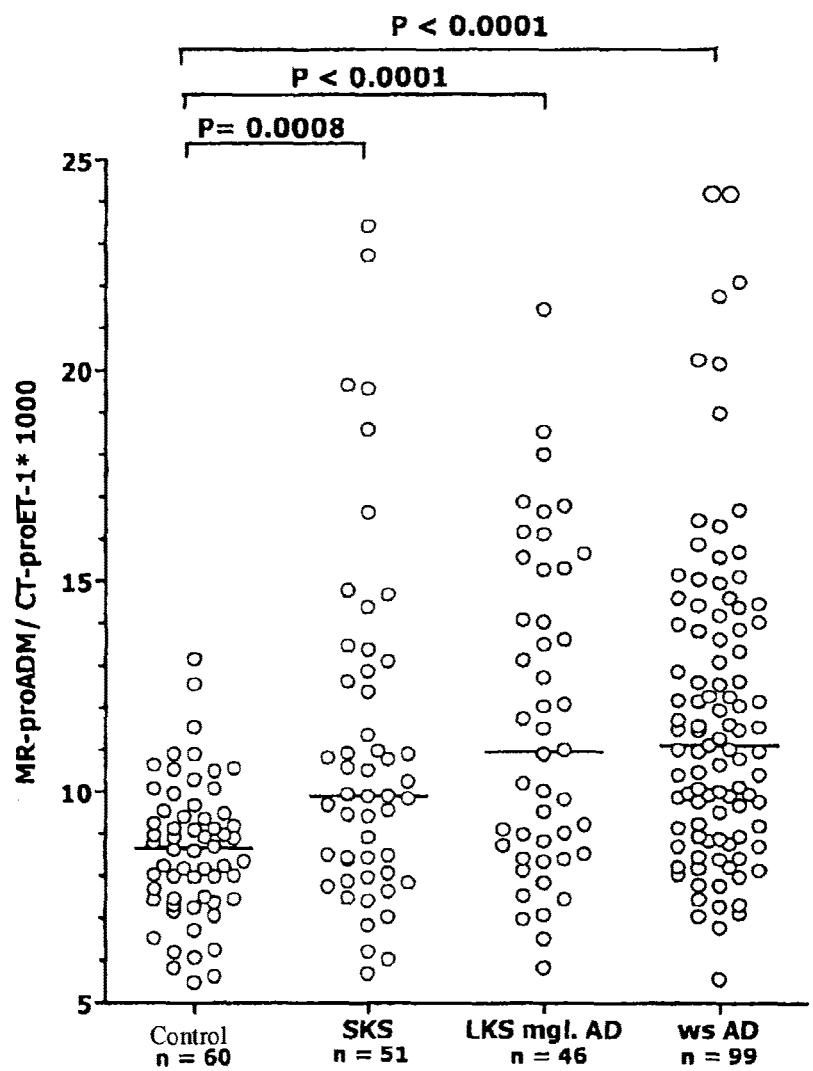
FIG. 5 shows the results of a common computational evaluation of the measured results, shown in FIG. 2, for the MR-proADM concentrations when these were related by calculating the quotient to the measured results for the CT-proET-1 concentrations in the same individual patients, shown in FIG. 3, in particular once again of 60 healthy control persons and of 196 patients with cognitive disturbances of various severities, who corresponded to the abovementioned groups (b), (c) and (d), i.e. the groups "SCD" (51 patients), "MCD pos AD" (46 patients) and "pr AD" (99 patients).

The measured MR-proANP, MR-proADM or CT-proET-1 concentrations in the plasma of healthy controls and patients with cognitive disturbances are shown in FIGS. 1 to 3. FIGS. 4 and 5 show the values which are obtained if the MR-proANP or MR-proADM concentrations are related to the associated CT-proET-1 concentrations (divided by the CT-proET-1 concentrations).

The numerical values determined in the form of the so-called medians for the various patient groups are shown in Table 1.

TABLE 1

| MARKER or MARKER COMBINATION | Median Controls | Median SCD | Median MCD pos AD | Median pr AD |
|---|---|---|---|---|
| MR-proANP (pmol/l) | 62.3 | 81.5 | 103.0 | 98.8 |
| MR-pro-ADM (nmol/l) | 0.60 | 0.64 | 0.69 | 0.71 |
| MR-proET-1 (pmol/l) | 68.0 | 60.40 | 59.5 | 61.8 |
| MR-proADM/-CTproET-1 × 1000 | 8.67 | 9.91 | 10.96 | 11.10 |
| MR-proANP/CT-proET-1 | 0.97 | 1.32 | 1.64 | 1.69 |

The specificities and sensitivities calculated from the measured values according to FIGS. 1 to 5 using the values stated in each case for the cut-off, in particular for the various patient groups, are shown in Table 2, in which the values obtained if the product of the concentrations for MR-proANP and those for MR-proADM is calculated (MR-proANP×MRproADM) or if this product is additionally divided by the associated CT-proET-1 concentrations were additionally recorded.

TABLE 2

| MARKER or MARKER COMBINATION | Cut-off (pmol/l) | Specificity (%) | Sensitivity SCD (%) | Sensitivity MCD pos AD (%) | Sensitivity pr AD (%) |
|---|---|---|---|---|---|
| MR-proANP | 87.0 pmol/l | 80.0 | 43.1 | 58.7 | 64.7 |
| MR-proADM | 0.7 nmol/l | 80.0 | 37.3 | 50.0 | 50.5 |
| CT-proET1 | 59.5 pmol/l | 80.0 | 49.0 | 52.2 | 45.5 |
| MR-pro-ADM/CT-proET1 × 1000 | 10.0 | 80.0 | 47.1 | 56.5 | 62.6 |
| MR-pro-ANP/CT-proET1 | 1.15 | 80.0 | 68.3 | 76.1 | 80.8 |
| MR-proANP × MR-proADM | 58.5 | 80.0 | 39.2 | 56.5 | 63.6 |
| MR-proANP × MR-pro-ADM/CT-proET1 × 1000 | 0.72 | 80.0 | 58.8 | 71.7 | 79.8 |

The values in Table 1 and in the corresponding figures show that in particular the MR-proANP concentrations, but also the MR-proADM concentrations, clearly increase with the severity of the symptoms in the direction:

Controls<SCD<MCD pos AD≤pr AD as is evident from the values for the medians of the various patient groups. It is furthermore evident that the trend, which is already recognizable in the individual determinations of MR-proANP or MR-proADM, is further illustrated if the measured values are divided by the associated CT-proET-1 concentrations measured for the same patient in each case.

Table 2 shows that, in the determination of individual analytes, the highest sensitivity of 64.7% is obtained in the determination of MR-proANP for the patient group "probably Alzheimer's disease" (pr AD) but that the sensitivity is further considerably improved and reaches a value of 80.8% for the group "pr AD" if the measured values are related to the associated CT-proET-1 concentrations.

Preliminary exploratory determinations of the concentrations of BNP (using a commercial NT-proBNP kit from Roche Diagnostics) in the case of patients from the same patient groups and relation of the values obtained to the patient-specific measured values (concentrations in pmol/l) for CT-ET-1 by division gave similar improvements to those in the measurement of MR-proANP, i.e. the measured values for BNP, too, became more informative as a result of division by the CT-ET-1 concentrations.

In the determination of MR-proADM, a similar improvement in the sensitivity is obtained (62.6% compared with 50.5%) in the case of a corresponding procedure.

Calculation of the product MR-proANP×MR-proADM results in no significant change compared with the values for the best individual analyte MR-proANP but in this case too, a clear improvement as above is obtained when said product is related to the measured values for the CT-proET-1 concentrations.

Although increased release of vasotropic peptides, for example of ANP, measured as MR-proANP concentration, or of ADM, measured as MR-proADM, is measurable also in the case of other diseases (sepsis, cardiovascular diseases/cardiac insufficiency; however, these can as a rule be easily differentiated from dementias) and vasotropic peptides are therefore not brain-specific parameters in the narrower sense, the determination of vasotropic peptides, in particular as a combination of the determination of vasodilatory peptides with a simultaneous determination of a suitable vasoconstrictive peptide, such as CT-pro-ET-1, is very suitable for purposes of the diagnosis of dementias, in particular for supportive early AD diagnosis, on the basis of the high specificity and the clearly differentiable sensitivities.

References

1. SELKOE D. J. (2001). Alzheimer's disease: genes, proteins, and therapy. Physiological Reviews 81: 741-766
2. Boetsch T., Stübner S. Auer S., Klinisches Bild, Verlauf und Prognose, Chapter 5 in: Hampel, Padberg, Möller (Eds.), Alzheimer Demenz—Klinische Verläufe, diagnostische Möglichkeiten, moderne Therapiestrategien; WVG mbH Stuttgart 2003
3. Boetsch T., Operationalisierte Demenzdiagnostik, Chapter 6.1 in: Hampel, Padberg, Möller (Eds.), Alzheimer Demenz—Klinische Verläufe, diagnostische Möglichkeiten, moderne Therapiestrategien; WVG mbH Stuttgart 2003
4. Reisberg B., Ferris S. H., de Leon M. J., Crook T., 1982, The global deterioration scale for assessment of primary degenerative dementia, Am J Psychiatry 139:1136-1139
5. McKhann G., Drachmann D., Folstein M., Katzman R., Price D., Stadlan E. M. 1984, Clinical diagnosis of Alzheimer's disease: Report of the NINCDS-ARDA work group under the auspices of department of health services task force on Alzheimer's disease, Neurology 24: 939-944
6. MCKEITH I. G. (2002), Dementia with lewy bodies. British Journal of Psychiatry 180: 144-147
7. GROWDON J. H., SELKOE D. J., ROSES A., TROJANOWSKI J. Q., DAVIES P., APPEL S. et al. [Working Group Advisory Committee] (1998), Consensus report of the Working Group on Biological Markers of Alzheimer's Disease. [Ronald und Nancy Reagan Institute of the Alzheimer's Association and National Institute on Aging Working Group on Biological Biomarkers of Alzheimer's Disease]. Neurobiology of Aging 19: 109-116
8. FRANK R. A., GALASKO D., HAMPEL H., HARDY J., DE LEON M. J., MEHTA P. D., ROGERS J., SIEMERS E., TROJANOWSKI J. Q. (2003), Biological markers for therapeutic trials in Alzheimer's disease. Proceedings of the biological markers working group; NIA initiative on neuroimaging in Alzheimer's disease. Neurobiology of Aging 24: 521-536
9. TEUNISSEN C. E., DE VENTE J., STEINBUSCH H. W. M., DE BRUIJN C. (2002). Biochemical markers related to Alzheimer's dementia in serum and cerebrospinal fluid. Neurobiology of Aging 23:485-508

10. I. M. KEITH (2000), The Role of Endogenous Lung Neuropeptides in Regulation of the Pulmonary Circulation. Physiol. Res. 49:519-537
11. ALBERTUS BEISHUIZEN, KOEN J. HARTEMINK, ISTVAN VERMES, AB JOHAN GROENEVELD (2005), Circulating cardiovascular markers and mediators in acute illness: an update. Clinica Chimica Acta 354 (2005) 21-34
12. NILS G. MORGENTHALER, JOACHIM STRUCK, BARBARA THOMAS, ANDREAS BERGMANN, Immunoluminometric Assay for the Midregion of Pro-Atrial Natriuretic Peptide in Human Plasma, Clinical Chemistry 50:1, 2004, 234-236.
13. NILS G. MORGENTHALER, JOACHIM STRUCK, CHRISTINE ALONSO, ANDREAS BERGMANN, Measurement of Midregional Proadrenomedullin in Plasma with an Immunoluminometric Assay, Clinical Chemistry 51:10, 2005, 1823-1829
14. JANA PAPASSOTIRIOU, NILS G. MORGENTHALER, JOACHIM STRUCK, CHRISTINE ALONSO, ANDREAS BERGMANN, Immunoluminometric Assay for Measurement of the C-Terminal Endothelin-1 Precursor Fragment in Human Plasma, Clinical Chemistry 52:6, 2006, 1144-1151
15. TARKOWSKI E. (2002). Cytokines in dementias. Current Drug Targets—Inflammation and Allergy 1: 193-200
16. TARKOWSKI E., LILJEROTH A. M., MINTHON L., TARKOWSKI A., WALLIN A., BLENNOW K. (2003), Cerebral pattern of pro- and anti-inflammatory cytokines in dementias. Brain Research Bulletin 61: 255-260
17. CHU D. Q., SMITH D. M., BRAN S. D. (2001), Studies of the microvascular effects of adrenomedullin and related peptides. Peptides 22:1881-1886
18. Karin Nilsson, Lars Gustayson, Björn Hultberg, Plasma Homocystein Concentration and Its Relation to Symptoms of Vascular Disease in Psychogeriatric Patients, Dement Geriatr Cogn Disord 2005; 20:35-41
19. M. D. Albadalejo, M. Antem, I. Pastor, C. Ruiz, R. Gonzalez-Aniorte, M. Asensio, Determinacion plasmatica de peptidos natriureticosen dementes, Rev Neurol 1997; 25 (139)
20. NILS G. MORGENTHALER, JOACHIM STRUCK, CHRISTINE ALONSO, ANDREAS BERGMANN, Assay for the Measurement of Copeptin, a Stable Peptide Derived from the Precursor of Vasopressin, Clinical Chemistry 52:1, 2006, 112-119

The invention claimed is:

1. A method for the detection and determination of Alzheimer's disease in a patient who is suffering from subjectively or objectively detectable cognitive disturbances potentially associated with Alzheimer's disease, the method comprising:
   (a) detecting and quantitating in a plasma or serum sample from the patient at least one vasodilatory peptide selected from the group consisting of atrial natriuretic peptides ANP and adrenomedullin (ADM), wherein the concentration of ANP is determined by measuring the amount of a midregional segment of proANP (MR-proANP) and the concentration of ADM is determined by measuring the amount of a midregional proADM (MR-proADM) fragment consisting of amino acids 45-92 of preproadrenomedullin;
   (b) detecting and quantitating in said sample the concentration of a vasoconstrictive peptide, endothelin-1 (ET-1), wherein the concentration of ET-1 peptide in said sample is determined by measuring the amount of a C-terminal proET-1 fragment (CTproET-1) consisting of amino acids 168-212 of pre-proendothelin-1; and
   (c) determining a ratio index of the concentration(s) of the one or more vasodilatory peptide(s) to the concentration of the endothelin-1 peptide, wherein a ratio index above the corresponding ratio index determined for healthy controls is indicative of Alzheimer's disease,
   wherein at least one of step (a) and step (b) comprises an immunoassay.

2. The method of claim 1, wherein the ratio index is the ratio index MR-proADM/CT-proET1, wherein the concentrations of MR-proADM and CT-proET1 are determined in pmol/l and a ratio index of more than 10.0 is indicative for Alzheimer's disease.

3. The method of claim 1, wherein the ratio index is the ratio index MR-proANP/CT-proET1, wherein the concentrations of MR-proANP and CT-proET1 are determined in pmol/l and a ratio index of more than 1.15 is indicative for Alzheimer's disease.

4. The method of claim 1, wherein the ratio index is the ratio index MR-proANP×MR-proADM/CT-proET1, wherein the concentrations of MR-proANP, MR-proADM and CT-proET1 are determined in pmol/l and a ratio index of more than 0.72 is indicative for Alzheimer's disease.

5. The method of claim 1, wherein step a) comprises an immunoassay.

6. The method of claim 1, wherein step b) comprises an immunoassay.

7. The method of claim 1, wherein both steps a) and b) comprise immunoassays.

* * * * *

UNITED STATES PATENT AND TRADEMARK OFFICE
CERTIFICATE OF CORRECTION

PATENT NO. : 8,916,388 B2  
APPLICATION NO. : 12/305088  
DATED : December 23, 2014  
INVENTOR(S) : Bergmann et al.

It is certified that error appears in the above-identified patent and that said Letters Patent is hereby corrected as shown below:

On the Title Page

In the Assignee (73): Delete "Sphingotec GmbH" and insert -- B.R.A.H.M.S GmbH --

Signed and Sealed this  
Fourteenth Day of April, 2015

Michelle K. Lee  
*Director of the United States Patent and Trademark Office*